United States Patent [19]
Pauly

[11] Patent Number: 6,141,592
[45] Date of Patent: Oct. 31, 2000

[54] DATA TRANSMISSION USING A VARYING ELECTRIC FIELD

[75] Inventor: Robert L. Pauly, Friendswood, Tex.

[73] Assignee: Intermedics Inc., Angleton, Tex.

[21] Appl. No.: 09/036,528

[22] Filed: Mar. 6, 1998

[51] Int. Cl.[7] .................................................. A61N 1/00
[52] U.S. Cl. .................................................. 607/60
[58] Field of Search .................................. 607/60, 32, 4

[56] References Cited

U.S. PATENT DOCUMENTS

| | | |
|---|---|---|
| 4,763,340 | 8/1988 | Yoneda et al. . |
| 4,787,389 | 11/1988 | Tarjan .......................................... 607/4 |
| 5,058,581 | 10/1991 | Silvian ....................................... 607/32 |
| 5,591,217 | 1/1997 | Barreras . |
| 5,654,984 | 8/1997 | Hershbarger et al. . |

FOREIGN PATENT DOCUMENTS 3331772  3/1985  Germany .

WO94/11977  5/1994  WIPO .

*Primary Examiner*—Scott M. Getzow
*Attorney, Agent, or Firm*—Schwegman, Lundberg, Woessner & Kluth, P.A.

[57] ABSTRACT

A system for communicating information between a first medical device and a second medical device. A first transducer is connected to the first medical device. A second transducer is connected to the second medical device. Each of the transducers includes a pair of electrically separated electrodes. A means is provided for imposing an electrical potential across one pair of electrodes of one of the transducers and modulating the electrical potential according to the information to be communicated, to generate a modulated electric field. The other of the transducers is disposed within influence of the modulated electric field. A means is provided having inputs connected to the pair of electrodes of the other of the transducers for amplifying an electrical potential sensed between the pair of electrodes of the other of the transducers.

21 Claims, 3 Drawing Sheets

DATA TRANSMISSION USING A VARYING ELECTRIC FIELD

BACKGROUND OF THE INVENTION

1. Field of the Invention

This invention relates generally to implantable medical devices and relates more particularly to arrangements for communicating data between a first medical device and an associated second medical device.

2. Background Information

Modern implantable medical devices such as cardiac stimulators, including, inter alia, pacemakers and defibrillators, are controlled by programmable microprocessors that can be reprogrammed before and after implantation of the device in a patient. This permits the physician to change the parameters and modes of operation of the implantable device to suit the needs of the patient. Such devices also are capable of reporting various aspects of their own status as well as sensing various physiological parameters of the patient that are useful to the physician. Consequently, it is necessary to provide means for communicating information, such as instructions and data, to and from the implantable medical device, both before and after implantation. This is often accomplished with an associated non-implantable medical device, sometimes referred to as a programmer, that provides an appropriate interface to the physician. The physician interface includes input and output devices, such as keypads, light pens, display screens, and printers. The non-implantable device, or programmer, also includes an interface for communicating with the implantable medical device, such interface often taking the form of a wand that can be placed near the implantable medical device to provide communication over a short distance.

A commonly employed arrangement for providing communication over a short distance, both before and after implantation, involves coupling the implantable and non-implantable medical devices through a magnetic field generated by one or the other of the medical devices. The transmission of information between the devices is accomplished by modulating the magnetic field in such a way as to encode the information to be transmitted. Amplitude modulation, frequency modulation, pulse width modulation and pulse position modulation are commonly used means for modulating the magnetic field. In a typical arrangement, a coil of wire in the implantable medical device carries a transient current that is driven by a communications circuit within the implantable device and modulated according to the information to be encoded and transmitted from the implantable device to the non-implantable device. A varying magnetic field, modulated according to the information encoded therein, is generated by the transmitting coil for interception by a receiving coil of wire in the non-implantable medical device. The magnetic field generates a transient current in the receiving coil. The receiving coil is connected to appropriate amplifying, demodulating and decoding circuitry for processing the received transient current. Likewise, the coil of wire in the implantable device can function as a receiving coil for intercepting a magnetic field generated by the non-implantable device, in connection with appropriate amplifying, demodulating and decoding circuitry in the implantable device. As an alternative, separate transmitting and receiving coils can be used in either or both of the medical devices.

In the communications arrangement discussed above, the coupling between the respective coils of the implantable and non-implantable devices is primarily magnetic. A disadvantage of such arrangements is their sensitivity, over a relatively great distance, to noise from stray magnetic fields generated by medical equipment that is often present in health care facilities. The rate at which information can be communicated between the magnetically coupled coils of the implantable and non-implantable medical devices is limited by the presence of such magnetic noise. Also, the relatively high inductance of the coils limits the maximum frequency at which the magnetic field can be modulated, thereby also limiting the maximum rate at which information can be communicated. Another disadvantage is that a significant portion of the energy delivered to the transmission coil is dissipated as heat due to ohmic resistance of the coil wire. In the implantable device, the energy used for communication is usually drawn from a battery hermetically sealed within the implantable device, which battery also supplies the energy for the therapeutic stimulating pulses that are generated by the device. Consequently, it is important to minimize the energy consumed for communication purposes in order to preserve the therapeutic life span of the implantable device.

It would be desirable to provide an arrangement for communicating information over a short distance between a first medical device and a second medical device having improved immunity to ambient magnetic noise.

It also would be desirable to provide an arrangement for communicating information over a short distance between a first medical device and a second medical device that permits an increased rate of transmission of data.

Furthermore, it would be desirable to provide an arrangement for communicating information over a short distance between a first medical device and a second medical device that has improved energy efficiency.

These and other desirable advantages are provided by the present invention.

SUMMARY OF THE INVENTION

This invention uses an electric field for transmission of information between a first medical device and a second medical device. The electric field is generated and sensed by transducers each having a pair of electrodes.

Objects of the invention include providing increased speed of communication, increased immunity to noise from ambient magnetic and electric fields, and lower power consumption in battery powered medical devices. Other objects and advantages of the invention will be apparent from the following description of a preferred embodiment made with reference to the drawings.

According to one aspect of the present invention, a system for communicating information between a first medical device and a second medical device is provided. A first transducer is connected to the first medical device. A second transducer is connected to the second medical device. Each of the transducers includes a pair of electrically separated electrodes. A first means is provided for imposing an electrical potential across one pair of electrodes of one of said transducers and modulating said electrical potential according to the information to be communicated, to generate a modulated electric field. The other of the transducers is disposed within influence of the modulated electric field. A second means is provided having inputs connected to said pair of electrodes of the other of said transducers for amplifying an electrical potential sensed between the pair of electrodes of said other of the transducers.

DETAILED DESCRIPTION OF THE PREFERRED EMBODIMENT

Figure 1:
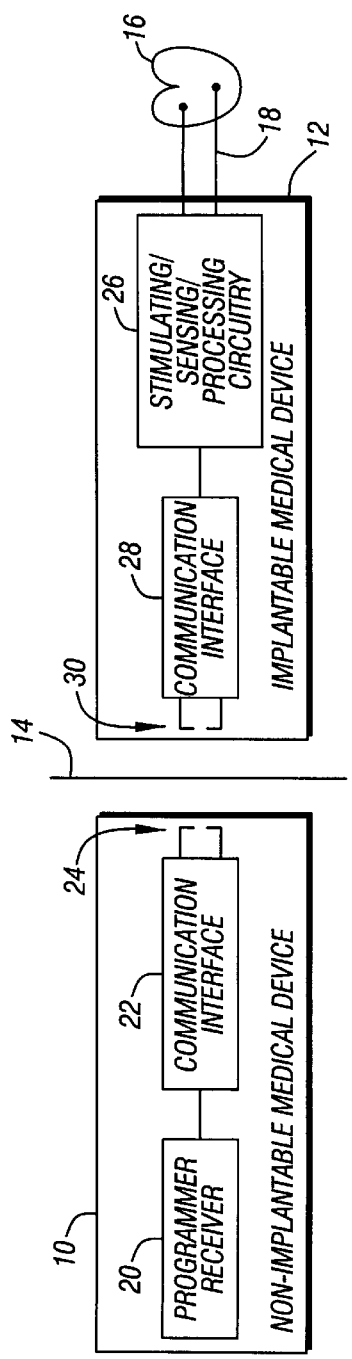
FIG. 1 is a block diagram of a system of implantable and non-implantable medical devices having means for communicating across a separation barrier.

Referring particularly to FIG. 1, there is illustrated a block diagram of a system for providing artificial cardiac stimulation. The system includes a first non-implantable medical device 10 and a second implantable medical device 12 that, ordinarily, are physically separated in use by a barrier 14 representing hermetic packaging or the surface of the human body. Non-implantable device 10 is a programmer that is located externally of the packaging, or human body, as the case may be, and is configured to issue commands to and receive information from implantable device 12 via telemetry. Implantable device 12 is a cardiac stimulator, such as a pacemaker or defibrillator, that ultimately is implanted in the human body in electrical communication with the heart 16 via one or more electrical leads and electrodes 18. During ordinary operation, implantable device 12, which is powered by a self-contained battery, operates under its own control and is not in proximity to non-implantable device 10. At the time of initial implantation of implantable device 12, however, and periodically thereafter, it is necessary to issue programming commands to device 12 to change operating modes or parameters, or to collect physiological or operational information sensed by implantable device 12. Therefore, from time to time non-implantable device 10 is placed in proximity to implantable device 12 and communication is commenced. Non-implantable device 10 can be understood as comprising a programmer/receiver portion 20, including a user interface such as an input device and a display screen, and a communications interface 22 including a transducer 24. Implantable device 12 can be understood as comprising stimulating/sensing/processing circuitry 26 in electrical communication with heart 16 via leads 18, and a communications interface 28 including a transducer 30. Transducer 24 of external device 10 can be located in a wand that can be placed near the implantable device 12 in relatively close proximity, but separated therefrom by an air gap, packaging, or human tissue. Communications interface 28 sends and receives binary data between itself and the communications interface 22 of non-implantable device 10 via a modulated electric field generated and received by transducers 30 and 24, respectively. Communications interface 28 is also in circuit communication with additional circuitry of the implantable device 12, designated generally as stimulating/sensing/processing circuitry 26, and sends and receives information between itself and the additional circuitry as binary data.

Communications interface 28 includes a transducer 30 and associated circuitry for applying an electrical potential across transducer 30, which potential is varied, i.e., modulated, according to an encoding scheme for encoding information to be transmitted from implantable device 12 to non-implantable device 10. In contrast to conventional transducers comprising a coil of wire in which a modulated transient current is imposed, transducer 30 comprises a pair of substantially planar conductors lying substantially in a common plane, separated and insulated by a dielectric film, each planar conductor being electrically connected to one pole of a two-pole variable voltage source. Each conductor may include multiple fingers or strips interdigitated with multiple fingers or strips of the other conductor, but all fingers or strips of a given conductor are electrically connected in common.

Similarly, communications interface 22 includes a transducer 24 and associated circuitry for applying an electrical potential across transducer 24, which potential is varied, i.e., modulated, according to an encoding scheme for encoding information to be transmitted from non-implantable device 10 to implantable device 12. As with transducer 30, transducer 24 comprises a pair of substantially planar conductors lying substantially in a common plane and separated by a dielectric, each planar conductor being electrically connected to one pole of a two-pole variable voltage source. Also as with transducer 30, each conductor of transducer 24 may include multiple fingers or strips interdigitated with multiple fingers or strips of the other conductor, but all fingers or strips of a given conductor are electrically connected in common. Because transducer 24 is not implanted, the dielectric may be simply air rather than an insulative film. If housed, transducer 24 should be located in a non-metallic housing.

For transmission, an electrical potential, modulated according to any conventional modulation scheme that encodes the information to be transmitted, is applied across one of the transducers 24 and 30. The applied electrical potential generates a reactive electrical near field between adjacent portions of the pair of planar conductors, which reactive electrical near field projects outwardly from the plane of the transmitting transducer. When modulated at a preferred rate of about 3 megaherz, the impedance of the transducer is high and very little current flows between the adjacent plates of the transducer.

For reception, the other one of the transducers 24 and 30 is placed within the influence of the reactive electric near field generated by the transmitting transducer. The generated electric field can be sensed by connecting the planar conductors of the receiving transducer to high impedance inputs of a voltage amplifier. The generated electric field varies in amplitude and direction according to the modulation of the driving voltage source, and consequently the electric field is sensed as a varying potential at the output of the voltage amplifier of the receiving device. Very little energy is lost in the form of ohmic heat as information is conveyed between the devices via a modulated electric field.

The transducers are relatively insensitive to magnetic fields and electric far fields, which results in a desirable level of immunity to noise from ambient magnetic and electric fields. Furthermore, because of the relatively low inductance and capacitance of the transducers at the radio frequencies of interest, the frequency at which the electric field can be modulated is significantly higher than the frequency at which a magnetic field, generated by a conventional transmitting coil, can be modulated.

Figure 2:
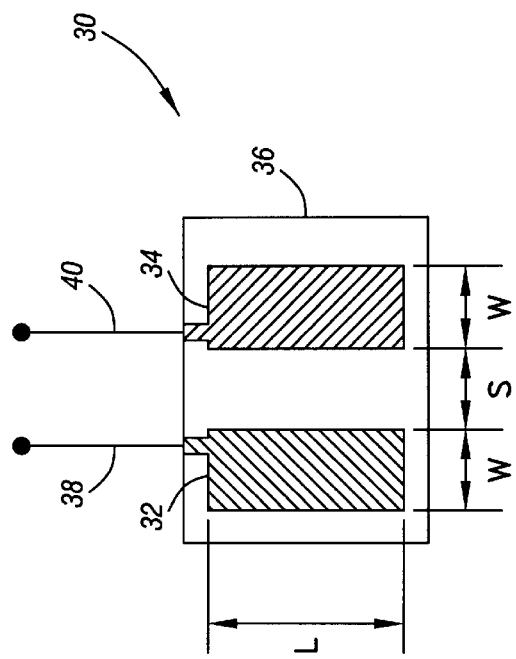
FIG. 2 is a plan view of a transducer useful in connection with the present invention.

Referring to FIG. 2, a preferred embodiment of transducer 30 is illustrated. Transducer 30 includes a pair of thin planar conductive plates 32 and 34, each comprising a rectangle having a width W and a length L and spaced from each other by a distance S with the longest sides parallel. The spacing distance S, as preferred, is equal to the width dimension W. As preferred, the length dimension L is about 1.4 inches, and the width and spacing dimensions, W and S, are about 0.6 inches. Plates 32 and 34 are disposed in a common plane, and are mounted on an insulative dielectric backing 36. As preferred, the insulative dielectric backing 36 comprises a thin film deposited directly on a metallic substrate such as the metal housing, or "can", of the implantable medical device 12, and the conductive plates 32 and 34 comprise conductive films deposited directly onto the dielectric backing 36. Another insulative dielectric film layer is deposited over plates 32 and 34 to prevent direct electrical contact between the plates and the electrolyte fluids of the human body. Each plate 32 and 34 is electrically connected to a respective insulated conductive lead 38 and 40, which leads are connected through appropriate feedthrough devices in the housing of the implantable medical device 12 to the circuitry of the communications interface 28.

Figure 3:
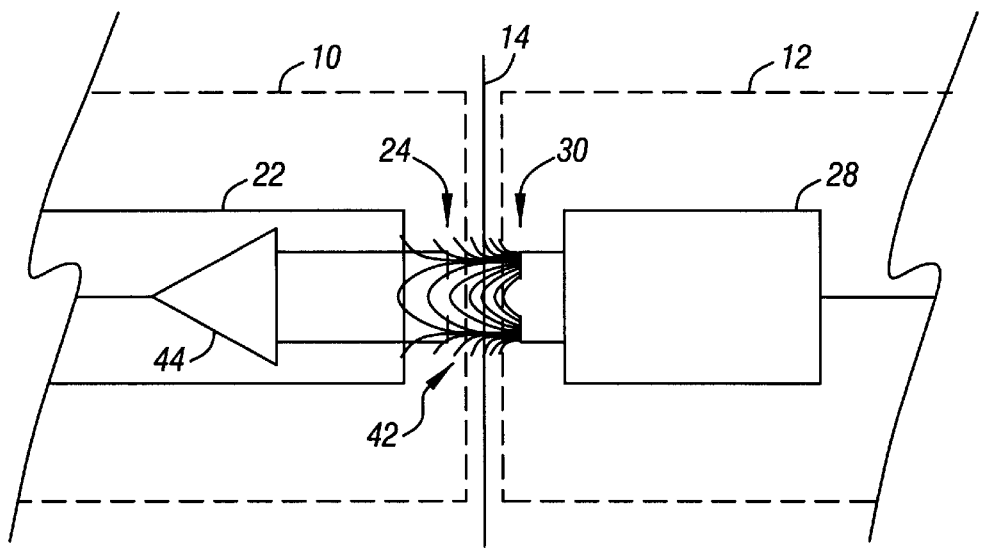
FIG. 3 is a partial block diagram of the communication portions of the system of medical devices of FIG. 1.

Referring to FIG. 3, a simplified block diagram of the telecommunications interface between the implantable medical device 12 and the non-implantable medical device 10 is illustrated. Information, originating in implantable device 12, is conveyed to communications interface 28 where the information is encoded in a modulated electrical potential that is applied between the plates of transducer 30. A reactive electric near field, represented by the electric field lines 42, is generated between the plates of transducer 30. The reactive electric near field extends outwardly from the plane of the plates of transducer 30, with the amplitude of the field diminishing with distance from the plates, as depicted by the increase in spacing between the electric field lines. The plates of receiving transducer 24 are disposed within the reactive electric near field generated by transducer 30, permitting the electric field to be sensed as an electrical potential between the plates of transducer 24. Each plate of transducer 24 is connected to a respective high-impedance input of a differential amplifier 44, whereby the electrical potential between the plates of transducer 24 is amplified to provide a signal suitable for further processing, demodulation, and decoding by additional circuitry of communications interface 22. While FIG. 3 depicts a static sample of the generated reactive electric near field, it should be understood that the amplitude and direction of the electric field is constantly changing in accordance with the modulation of the electrical potential applied between the plates of transmitting transducer 30. In essence, amplifier 44 provides an output signal that is representative of the time-varying nature of the electric field sensed at the plates of receiving transducer 24.

Again referring to FIG. 3, transducer 30 of the implantable medical device 12 typically would be disposed subdermally within a human body in proximity to electrolyte body fluids and body tissues perfused with electrolyte body fluids, but electrically isolated from such fluids by an insulative dielectric layer. Transducer 30 would be disposed externally of any metal housing of the implantable medical device and therefore would not be subject to Faraday shielding. Consequently, the space between transducer 30 and barrier 14 should be understood as being filled with electrolyte body fluids and body tissues, with barrier 14 representing the surface of the skin of the human body. Typically the distance between transducer 30 and the skin barrier 14 would be on the order of a few centimeters. In contrast, the space between barrier 14 and receiving transducer 24 should be understood as being filled with air, perhaps with one or more intermediate layers of non-conductive solid dielectric insulating material. No metallic layer should be interposed between the transducer 24 and transducer 30. The amplitude of the electric field is great in the vicinity between transducer 30 and skin barrier 14, but is sharply attenuated beyond the electrolyte-to-air interface at barrier 14. Nevertheless, using driving voltages well within the capability of battery powered devices, e.g., 3 volts, the amplitude of the electric field at reasonable distances beyond the barrier 14 is sufficiently great to be discerned as a potential between the plates of the receiving transducer and discriminated from background noise such that effective communication between the implantable and non-implantable devices is practical. Such communications, utilizing the medium of a varying electric field, can be conducted at rates of 3 megahertz or more, well above the practical rate limit of communications schemes employing magnetic coupling, with only minute amounts of battery power dissipated in generating the electric field.

Figure 4:
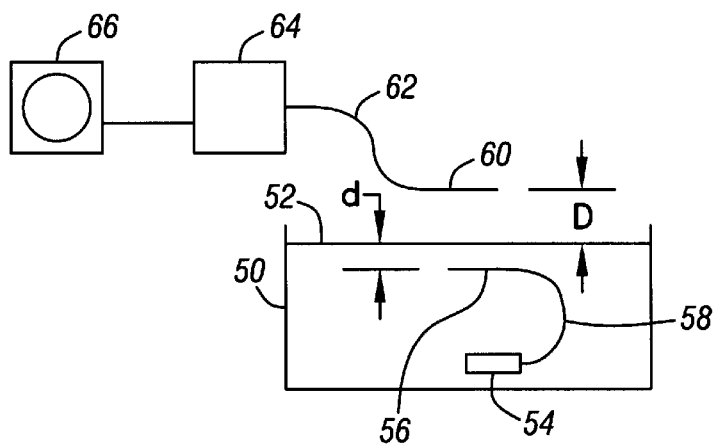
FIG. 4 is a schematic depiction of an experimental arrangement useful for demonstrating the principles of the present invention.

Referring to FIG. 4, an experimental arrangement is illustrated by which the feasibility of telecommunication between implanted and non-implanted medical devices, using a varying electric field, was demonstrated. A plastic tub 50 was filled with 0.9% saline solution 52, a saline solution electrolytically similar to body fluid. The saline solution 52 simulated the body fluid and tissue environment in which an implantable medical device would ordinarily reside during use. The surface of the saline solution 52 simulated the fluid-to-air interface of a human body at the surface of the skin. Submerged within solution 52 was a waterproof box 54 containing a battery powered oscillator circuit tuned to generate a square wave signal at 3 megahertz. The battery voltage was 4.5 volts, resulting in a 3 volt peak-to-peak output signal, which was applied to a transmitting transducer 56 via a twisted pair of insulated wires 58. Transducer 56 included two planar electrodes configured as illustrated in FIG. 2, and described above. The electrodes comprised rectangular copper traces on one side of a double-sided glass-epoxy etched circuit board. The underside of the circuit board transducer was fully covered in copper foil. The copper electrodes were insulated by a transparent silicone resin layer. All connections between the circuitry inside box 54 and the electrode plates of transducer 56 were well insulated such that the direct current resistance between the electrode plates and connecting wires 58, when immersed in saline solution 52, was infinite as measured by a digital multimeter. Transducer 56 was submerged a distance "d" below the surface of the saline solution 52. A second transducer 60, substantially identical to transducer 56, was suspended a distance "D" above the surface of saline solution 52, with the electrode plates facing downward. The electrode plates of transducer 60 were connected via a twisted pair of wires 62 to a tuned radio receiver 64. The input of receiver 64, to which wires 62 were connected, was tuned to 3 megahertz. The input frequency was converted in receiver 64 to an IF frequency of 455 kHz and applied through an internal bandpass filter to an internal IF amplifier stage having a gain of about 100 dB. The amplified IF output of receiver 64 was applied to the input of an oscilloscope 66, which was used to observe, measure and record the amplified and filtered signal from transducer 60. During the course of the experiment, the vertical spacing "D" between transducer 60 and solution 52 was varied, while the depth of submersion of transducer 56 remained constant and the amplitude of the driving signal applied to transducer 56 remained constant. The received signal amplitudes, as a function of spacing between transducers 56 and 60, are given in Table 1 and graphed in FIG. 5.

TABLE 1

| Transmitting Plate Distance Below Surface | Receiving Plate Distance Above Surface | Plate-to-Plate Horizontal Offset | Transmitted Signal Amplitude | Received Signal Amplitude |
|---|---|---|---|---|
| Transmitter On | | | | |
| 1" | 2" | 0" | 3.16 V | 106 mV |
| 1" | 3" | 0" | 3.16 V | 82 mV |
| 1" | 4" | 0" | 3.16 V | 60 mV |
| 1" | 5" | 0" | 3.16 V | 44 mV |
| 1" | 6" | 0" | 3.16 V | 32 mV |
| Transmitter Off | | | | |
| 1" | 6" | 0" | | 13 mV |

At a spacing of 6 inches between the receiving transducer 60 and the surface of saline solution 52, or in other words, at a transmitting transducer to receiving transducer spacing of 7 inches, the measured signal amplitude at the output of the tuned receiver and amplifier 64 was 32 mV, well above the background noise signal level of 13 mV as measured with the transmitting oscillator turned off. At a spacing of 2 inches between the receiving transducer 60 and the surface of saline solution 52, or at a transmitting transducer to receiving transducer spacing of 3 inches, the measured signal amplitude at the output of the tuned receiver and amplifier 64 was 106 mV. At the latter spacing, the waveform displayed on the oscilloscope revealed distortion indicative of saturation of the IF amplifier of receiver 64. Measurements at spacings less than 2 inches above the surface of saline solution 52 would have required reducing the gain of the IF amplifier.

Figure 6:
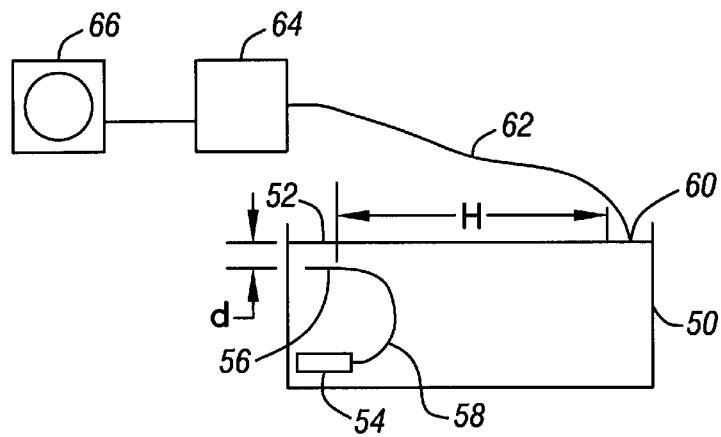
FIG. 6 is a schematic depiction of another experimental arrangement useful for demonstrating the principles of the present invention.

Referring to FIG. 6, a second experimental arrangement is illustrated by which the feasibility of telecommunication between implanted and non-implanted medical devices, using a varying electric field, was demonstrated. The arrangement of FIG. 6 is substantially similar to the arrangement described above with respect to FIG. 4, except for the placement of the receiving transducer 60. Transducer 56 was submerged a distance "d" below the surface of the saline solution 52. A second transducer 60, substantially identical to transducer 56, was suspended in contact with the surface of saline solution 52, with the electrode plates facing downward. The electrode plates of transducer 60 were connected via a twisted pair of wires 62 to a tuned radio receiver 64. The input of receiver 64, to which wires 62 were connected, was tuned to 3 megahertz. The input frequency was converted in receiver 64 to an IF frequency of 455 kHz and applied through an internal bandpass filter to an internal IF amplifier stage having a gain of about 100 dB. The amplified IF output of receiver 64 was applied to the input of an oscilloscope 66, which was used to observe, measure and record the amplified and filtered signal from transducer 60. During the course of the experiment, the vertical placement of the transducer 60 relative to solution 52 was held constant, the depth of submersion of transducer 56 remained constant, and the amplitude of the driving signal applied to transducer 56 remained constant. The center-to-center horizontal offset "H" of receiving transducer 60 relative to transmitting transducer 56 was varied. The amplified received signal amplitudes, as a function of horizontal offset between transducers 56 and 60, are given in Table 2 and graphed in FIG. 7.

TABLE 2

| Transmitting Plate Distance Below Surface | Receiving Plate Distance Above Surface | Plate-to-Plate Horizontal Offset | Transmitted Signal Amplitude | Received Signal Amplitude |
|---|---|---|---|---|
| Transmitter On | | | | |
| 1" | 1" | 5" | 3.16 V | 106 mV |
| 1" | 1" | 6" | 3.16 V | 85 mV |
| 1" | 1" | 7.5" | 3.16 V | 65 mV |
| 1" | 1" | 9.5" | 3.16 V | 58 mV |

At a vertical spacing of one inch and a horizontal center-to-center offset of 9.5 inches between the receiving transducer 60 and the transmitting transducer 56, the measured signal amplitude at the output of the tuned receiver and amplifier 64 was 58 mV, well above the background noise signal level of 13 mV, measured with the transmitting oscillator turned off. At a horizontal offset of 5 inches between the receiving transducer 60 and the transmitting transducer 56, the measured signal amplitude at the output of the tuned receiver and amplifier 64 was 106 mV. At the latter spacing, the waveform displayed on the oscilloscope revealed distortion indicative of saturation of the IF amplifier of receiver 64. Measurements at spacings less than 5 inches horizontal offset between the receiving and transmitting transducers 60 and 56, respectively, would have required reducing the gain of the IF amplifier.

Figure 5:
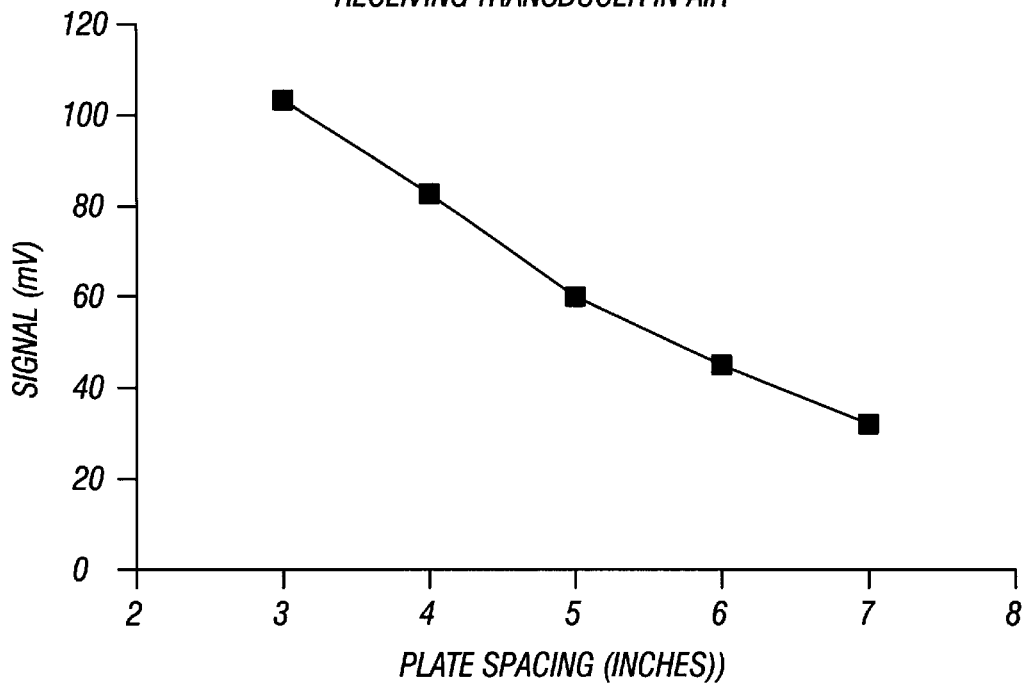
FIG. 5 is a graph of data collected using the experimental arrangement of FIG. 4.
Figure 7:
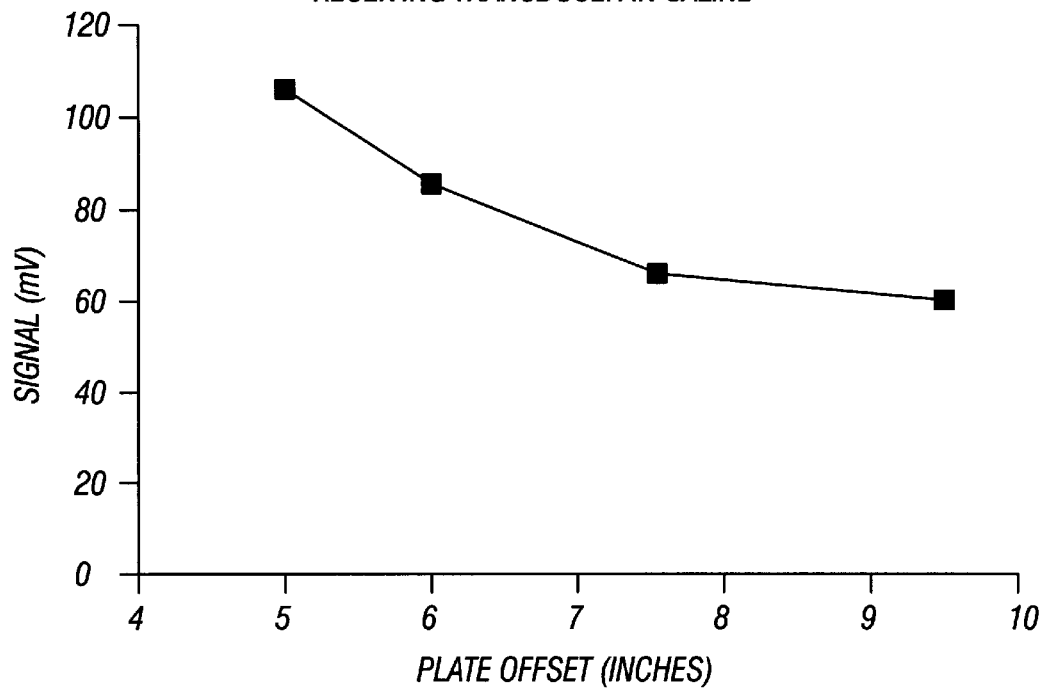
FIG. 7 is a graph of data collected using the experimental arrangement of FIG. 6.

From the experimental results shown in Tables 1 and 2 and FIGS. 5 and 7, as gathered with the experimental arrangements shown in FIGS. 4 and 6, it appears that the amplitude of the received signal decreases with distance, but does so asymptotically. Extrapolation of the experimental results suggests that useful signal amplitude can be discerned above the background noise at significant air gaps of many inches between the surface of the skin and the receiving transducer. The experimental results also suggest that useful signal amplitude can be discerned above the background noise at significant horizontal displacements of many inches between the transmitting and receiving transducers where one transducer is implanted subdermally and the other is in contact with the surface of the skin. Consequently, the contact transducer need not be located directly over the implanted transducer. This provides useful placement options in a clinical setting, where it may be desirable for the external transducer to be adhesively attached to the skin at a location remote from a pectoral or abdominal implant site. Such remote placement, e.g., on the shoulder, neck, arm, or hand, would permit communication with the implanted medical device without requiring the patient to be shaved or disrobed. Similarly, the transducer could be placed in contact with the skin at a location remote from the implant, e.g., on the back or palm of the hand, without use of adhesive. Use of the external transducer during surgery would be facilitated, for example, by placing it beneath the patient out of the sterile surgical field. In another variation, the medical devices in communication can both be non-implanted devices, such as a transmitter and a receiver for wireless communication of patient data within the operating room.

The present invention has been illustrated and described with particularity in terms of a preferred embodiment. Nevertheless, it should be understood that no limitation of the scope of the invention is intended. The scope of the invention is defined by the claims appended hereto. It should also be understood that variations of the particular embodiments described herein incorporating the principles of the present invention will occur to those of ordinary skill in the art and yet be within the scope of the appended claims.

I claim:

1. A system for communicating information between a first medical device and a second medical device comprising:

a first transducer connected to said first medical device;

a second transducer connected to said second medical device;

each of said transducers including a pair of electrically separated electrodes;

means for imposing an electrical potential across one said pair of electrodes of one of said transducers and modulating said electrical potential according to said information to be communicated, to generate a modulated electric field;

said other of said transducers being disposed within influence of the modulated electric field; and means having inputs connected to said pair of electrodes of said other of said transducers for amplifying an electrical potential sensed between said pair of electrodes of said other of said transducers.

2. The system of claim 1, in which one of said first and second medical devices is an implantable medical device.

3. The system of claim 2, in which the transducer connected to the implantable medical device is an implantable transducer.

4. The system of claim 1, in which said first medical device is hermetically sealed and powered by an internal battery.

5. The system of claim 4, in which said first medical device includes a metallic housing.

6. The system of claim 5, in which said first transducer is disposed externally of said metallic housing.

7. The system of claim 6, in which said pair of electrodes of the first transducer is attached to said metallic housing, and a dielectric layer is disposed intermediate said pair of electrodes and said housing.

8. The system of claim 7, in which said pair of electrodes of the first transducer comprise planar plate conductors.

9. The system of claim 8, in which said planar plate conductor are disposed substantially in a common plane.

10. A medical device, having means for communicating information between said medical device and another medical device, comprising:

a transducer including a pair of electrically separated electrodes;

an insulative dialectric covering said electrodes, said dialectric being adapted to prevent direct electrical contact between said electrodes and fluids of the body of a patient; and means for imposing an electrical potential across said pair of electrodes and modulating said electrical potential according to said information to be communicated, to generate a modulated electric field external of said medical device.

11. The medical device of claim 10, in which said medical device is an implantable medical device.

12. The medical device of claim 11, in which the transducer is an implantable transducer.

13. The medical device of claim 12, in which said medical device is hermetically sealed and powered by an internal battery.

14. The medical device of claim 13, in which said medical device includes a metallic housing.

15. The medical device of claim 14, in which said transducer is disposed externally of said metallic housing.

16. The medical device of claim 15, in which said pair of electrodes is attached to said metallic housing, and a portion of said dielectric is disposed intermediate said pair of electrodes and said housing.

17. The medical device of claim 16, in which said pair of electrodes comprise planar plate conductors.

18. The medical device of claim 17, in which said planar plate conductors are disposed substantially in a common plane.

19. A method of communicating information between an implantable medical device and a non-implantable medical device, said implantable medical device having a first transducer including a first pair of electrically separated electrodes, said non-implantable medical device having a second transducer including a second pair or electrically separated electrodes, at least one of said implantable and said non-implantable medical devices having means for imposing an electrical potential across said respective pair of electrodes of said respective transducers and modulating said electrical potential according to said information to be communicated to generate a modulated electric field, at least another of said implantable and said non-implantable medical devices having means including inputs connected to said respective pair of electrodes for amplifying an electrical potential sensed between said respective pair of electrodes, comprising the steps of:

a) implanting said implanted medical device subdermally; and b) placing said transducer of said non-implantable medical device on the dermis.

20. An implantable medical device, having means for communicating information between said medical device and another medical device, comprising:

a hermetically sealed metallic housing;

an internal battery inside said housing for powering said medical device;

a transducer including a pair of electrically separated electrodes, said pair of electrodes comprising planar plate conductors and being attached to said metallic housing, and a dielectric layer being disposed intermediate said pair of electrodes and said housing; and means for imposing an electrical potential across said pair of electrodes and modulating said electrical potential according to said information to be communicated, to generate a modulated electric field external of said medical device.

21. The medical device of claim 20, in which said planar plate conductors are disposed substantially in a common plane.

* * * * *